United States Patent
Burns et al.

(10) Patent No.: US 7,890,155 B2
(45) Date of Patent: Feb. 15, 2011

(54) FEATURE EMPHASIS AND CONTEXTUAL CUTAWAYS FOR IMAGE VISUALIZATION

(75) Inventors: Michael Burns, Princeton, NJ (US); Martin Haidacher, Rauris (AT); Wolfgang Wein, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 573 days.

(21) Appl. No.: 11/904,965

(22) Filed: Sep. 28, 2007

(65) Prior Publication Data

US 2008/0167551 A1 Jul. 10, 2008

Related U.S. Application Data

(60) Provisional application No. 60/883,382, filed on Jan. 4, 2007.

(51) Int. Cl.
*A61B 5/05* (2006.01)
(52) U.S. Cl. .................. 600/407; 600/424; 600/462; 600/466
(58) Field of Classification Search .............. 600/407, 600/424, 462, 466
See application file for complete search history.

(56) References Cited

U.S. PATENT DOCUMENTS 6,961,405 B2 * 11/2005 Scherch ................... 378/65

2006/0036167 A1 * 2/2006 Shina ..................... 600/433
2006/0149134 A1 * 7/2006 Soper et al. ............. 600/182
2006/0241465 A1 * 10/2006 Huennekens et al. ...... 600/458

OTHER PUBLICATIONS

S. Bruckner, S. Grimm, A. Kanitsar, and M. E. Groller. Illustrative context-preserving exploration of volume data. IEEE Transactions on Visualization and Computer Graphics, 12(6) :1559-1569, 2006.
S. Bruckner and M. E. Groller. VolumeShop: An interactive system for direct volume illustration. In Proceedings of IEEE Visualization'05, pp. 671-678, 2005. http://www.volumeshop.org/.
S. Bruckner and M. E. Groller. Exploded views for volume data. IEEE Transactions on Visualization and Computer Graphics, 12(5) :1077-1084, 2006.
C. Correa, D. Silver, and M. Chen. Feature aligned volume manipulation for illustration and visualization. IEEE Transactions on Visualization and Computer Graphics, 12(5) :1069-1076, 2006.
H. Doleisch, M. Gasser, and H. Hauser. Interactive feature specification for focus+context visualization of complex simulation. In Proceedings of VisSym'03, pp. 239-248, 2003.

(Continued)

*Primary Examiner*—Long V Le
*Assistant Examiner*—Nicholas L Evoy
(74) *Attorney, Agent, or Firm*—Donald B. Paschburg; F. Chau & Associates, LLC

(57) ABSTRACT

A method for visualizing one or more objects of interest within a volume of imaging data includes the steps of receiving a volume of imaging data and displaying the one or more objects of interest within the volume by adaptively changing the amount of information displayed from the volume based on (1) a viewing direction of the volume, (2) a position of the one or more objects of interest within the volume, and (3) importance values of materials within the volume.

13 Claims, 5 Drawing Sheets

OTHER PUBLICATIONS

A. Gooch, B. Gooch, P. Shirley, and E. Cohen. A non-photorealistic lighting model for automatic technical illustration. In SIGGRAPH '98: Proceedings of the 25th annual conference on Computer graphics and interactive techniques, pp. 447-452, 1998.

H. Hauser. Scientific Visualization: The Visual Extraction of Knowledge from Data, chapter Generalizing Focus+Context Visualization, pp. 305-327. Springer, 2005.

H. Hauser and M. Mlejnek. Interactive volume visualization of complex flow semantics. In Proceedings of VMV '03, pp. 191-198, 2003.

H. Hauser, L. Mroz, G. I. Bischi, and M. E. Groller. Two-level volume rendering. IEEE Transactions on Visualization and Computer Graphics, 7(3):242-252, 2001.

A. Konig, H. Doleisch, and M. E. Groller. Multiple views and magic mirrors—fMRI visualization of the human brain. In Proceedings of SCCG '99, pp. 130-139, 1999.

A. Kruger, C. Tietjen, J. Hintze, B. Preim, I. Hertel, and G. Strauβ. Interactive visualization for neck dissection planning. In Proceedings of EuroVis'05, pp. 295-302, 2005.

J. Kruger, J. Schneider, and R. Westermann. Clearview: An interactive context preserving hotspot visualization technique. IEEE Transactions on Visualization and Computer Graphics, 12(5):941-948, 2006.

C. Rezk-Salama and A. Kolb. Opacity peeling for direct volume rendering. Computer Graphics Forum, 25(3):597-606, 2006.

M. Straka, M. Cervenansky, A. La Cruz, A. Kochl, M. Sramek, M. E. G roller, and D. Fleischmann. The VesselGlyph: Focus & context visualization in CT-angiography. In Proceedings of IEEE Visualization'04, pp. 385-392, 2004.

K. Hinrichs, T. Ropinski, F. Steinicke. Visual exploration of seismic volume datasets. In Proceedings of the WSCG '06, pp. 73-80, 2006.

I. Viola and M. E. Groller. Smart visibility in visualization. In Proceedings of Computational Aesthetics in Graphics, Visualization and Imaging, pp. 209-216, 2005.

I. Viola, A. Kanitsar, and M. E. Groller. Importance-driven feature enhancement in volume visualization. IEEE Transactions on Visualization and Computer Graphics, 11(4): 408-418, 2005.

W. Wein, B. Roper, and N. Navab. Automatic registration and fusion of ultrasound with CT for radiotherapy. In Proceedings of MICCAI '05, Lecture Notes in Computer Science. Springer, 2005.

* cited by examiner (a)           (b)           (c)

(a) (b)

FEATURE EMPHASIS AND CONTEXTUAL CUTAWAYS FOR IMAGE VISUALIZATION

CROSS-REFERENCE TO RELATED APPLICATIONS

This application claims priority to U.S. Provisional Application No. 60/883,382, filed on Jan. 4, 2007, the disclosure of which is incorporated by reference herein.

BACKGROUND OF THE INVENTION

1. Technical Field

The present disclosure relates to three-dimensional (3D) visualization of imaging data, and more particularly to methods and systems for visualizing imaging data using importance values that do not require segmentation.

2. Discussion of Related Art

Users have turned to computers to assist them in the examination and analysis of images of real-world data because of the increasingly fast processing power of modern day computers. For example, within the medical community, radiologists and other professionals who once examined x-rays hung on a light screen now use computers to examine images obtained via computed tomography (CT), computed tomography angiography (CTA), magnetic resonance (MR), ultrasonography, positron emission tomography (PET), single photon emission computed tomography (SPECT), magnetic source imaging, and other imaging techniques. Countless other imaging techniques will no doubt arise as medical imaging technology evolves.

Each of the above identified imaging procedures generates volume images, although each relies on a different technology to do so. Thus, CT requires an x-ray source to rapidly rotate around a patient to obtain up to hundreds of electronically stored pictures of the patient. Conversely, for example, MR requires that radio-frequency waves be emitted to cause hydrogen atoms in the body's water to move and release energy, which is then detected and translated into an image. Because each of these techniques penetrates the body of a patient to obtain data, and because the body is three-dimensional, this data represents a three-dimensional image, or volume. In particular, CT and MR both provide three-dimensional "slices" of the body, which can later be electronically reassembled.

Computer graphics images, such as medical images, have typically been modeled through the use of techniques such as surface rendering and other geometric-based techniques. Because of known deficiencies of such techniques, volume-rendering techniques have been developed as a more accurate way to render images based on real-world data. Volume-rendering takes a conceptually intuitive approach to rendering, by assuming that three-dimensional objects are composed of basic volumetric building blocks.

While many physicians still prefer cross-sectional slice images for diagnosis and interpretation of the data, volume rendering can provide a better global spatial impression of the anatomy. This becomes especially important for fusion of CT/CTA with interventional imaging modalities.

In medical procedures such as biopsy and radio frequency ablation, the insertion path of a needle must be carefully planned on the CT scan to avoid critical structures in the patient. During a procedure, ultrasound may be used as an interventional imaging modality to assist in navigating the needle(s) to the correct location. Medical ultrasound mainly depicts borders between various tissue types in a 2D plane oriented from the transducer into the patient's body. If a tracking system is used to locate the ultrasound probe in 3D, and the pre-operative CT scan is aligned (i.e. registered) correctly with the patient coordinate system, volume rendering of the CT data can be merged with a real-time view of the ultrasound plane. The dense 3D information from the CT data helps the physician to relate both the needle and ultrasound plane to the critical anatomical structures, right in the operating theater. Furthermore, planning information like ablation target volumes and margins, optimal needle path, etc., can be visualized.

However, it can be difficult to show enough data from the dense pre-operative scan without occluding the ultrasound image plane. Further, due to the mass of information in a single volume data set, it is preferred that an observer be directed to the most significant parts of the whole data set. Importance-driven rendering can be used to quickly enable cognition of important parts while retaining an impression of the position and the relation of these parts with respect to the rest of the data set. Currently, a data set including a segmentation of the different parts according to their spatial locations is required. However, segmenting a volume data set into different spatial areas is a time consuming and computationally intensive task, which may also require user intervention.

Thus, there exists a need for methods and systems for importance-driven rendering of an object of interest within a volume with minimal occlusion that does not require segmentation of a volume according to spatial locations of the segments.

SUMMARY OF THE INVENTION

According to an exemplary embodiment of the present invention there is provided a method for visualizing one or more objects of interest within a volume of imaging data. The method includes the steps of receiving the volume of imaging data, and displaying the one or more objects of interest within the volume by adaptively changing the amount of information displayed from the volume based on a viewing direction of the volume, a position of the one or more objects of interest within the volume, and user-specified importance values of materials within the volume. The volume of imaging data may include data from a three dimensional (3D) computed tomography (CT) scan.

The method may further include a step of using the display of the one or more objects of interest within the volume to aid a surgical procedure. A first one of the objects of interest may be a needle and the surgical procedure may include a step of guiding the needle into a second one of the objects of interest.

The method may further include shading the materials within the volume based on the corresponding importance values. The shading may be performed by various shading techniques, including, for example, Phong, Gooch, etc. The materials may represent different types of anatomical tissue structures within the volume.

The step of receiving the volume of imaging data may include steps of receiving two dimensional (2D) imaging data and registering the volume of imaging data with the 2D imaging data to generate the one or more objects of interest within the volume of imaging data. The 2D imaging data may include data from a tracked ultrasound image.

The step of displaying each object of interest may include steps of selecting a viewing angle that is relative to the viewing direction, determining regions of the volume that fall within the viewing angle, determining occlusion values for each point of the regions based on the degree that each point occludes the object of interest, and modifying an opacity value for each point based on the occlusion value of the point and a ranking of the material that the point corresponds to.

The step of determining the regions may include steps of determining a first region having a first angle away from the viewing direction, and determining a second region having a second angle away from the viewing direction. The first region has a bottom that is a first distance away from the object of interest. The second region has a bottom that is a second distance away from the object of interest. The first angle is less than the second angle and the first distance is less than the second distance. The first and second regions may be cone shaped.

According to an exemplary embodiment of the present invention there is provided a system for visualizing one or more objects of interest within a volume of imaging data. The system includes a memory, a processor, and a display unit. The memory stores a visualization program. The processor executes the visualization program. The display unit displays a modified image. The visualization program (1) receives the volume of imaging data and (2) displays a new image on the display by adaptively changing the amount of visible information from the volume based on (i) a viewing direction of the volume, (ii) a position of the one or more objects of interest within the volume, and (iii) importance values of materials within the volume.

The volume of imaging data may be registered with two-dimensional (2D) imaging data to generate the one or more objects of interest within the volume of imaging data. The system may further include a surgical tool administering device, which automatically applies a surgical tool to a structure of a patient based on the new image. One of the objects of interest represents the surgical tool and a second one of the objects of interest represents the structure. The surgical tool administering device may be a surgical robot.

These and other exemplary embodiments, aspects, features and advantages of the present invention will be described or become more apparent from the following detailed description of exemplary embodiments, which is to be read in connection with the accompanying figures.

BRIEF DESCRIPTION OF THE DRAWINGS

Exemplary embodiments of the invention can be understood in more detail from the following descriptions taken in conjunction with the accompanying drawings in which.

DETAILED DESCRIPTION OF THE EXEMPLARY EMBODIMENTS

In general, exemplary embodiments for systems and methods for visualizing one or more objects of within a volume of imaging data will now be discussed in further detail with reference to illustrative embodiments of FIGS. 1-7. This invention may, however, be embodied in different forms and should not be construed as limited to the embodiments set forth herein. Rather, these embodiments are provided so that this disclosure will be thorough and complete, and will fully convey the scope of the invention to those skilled in the art.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

Figure 1:
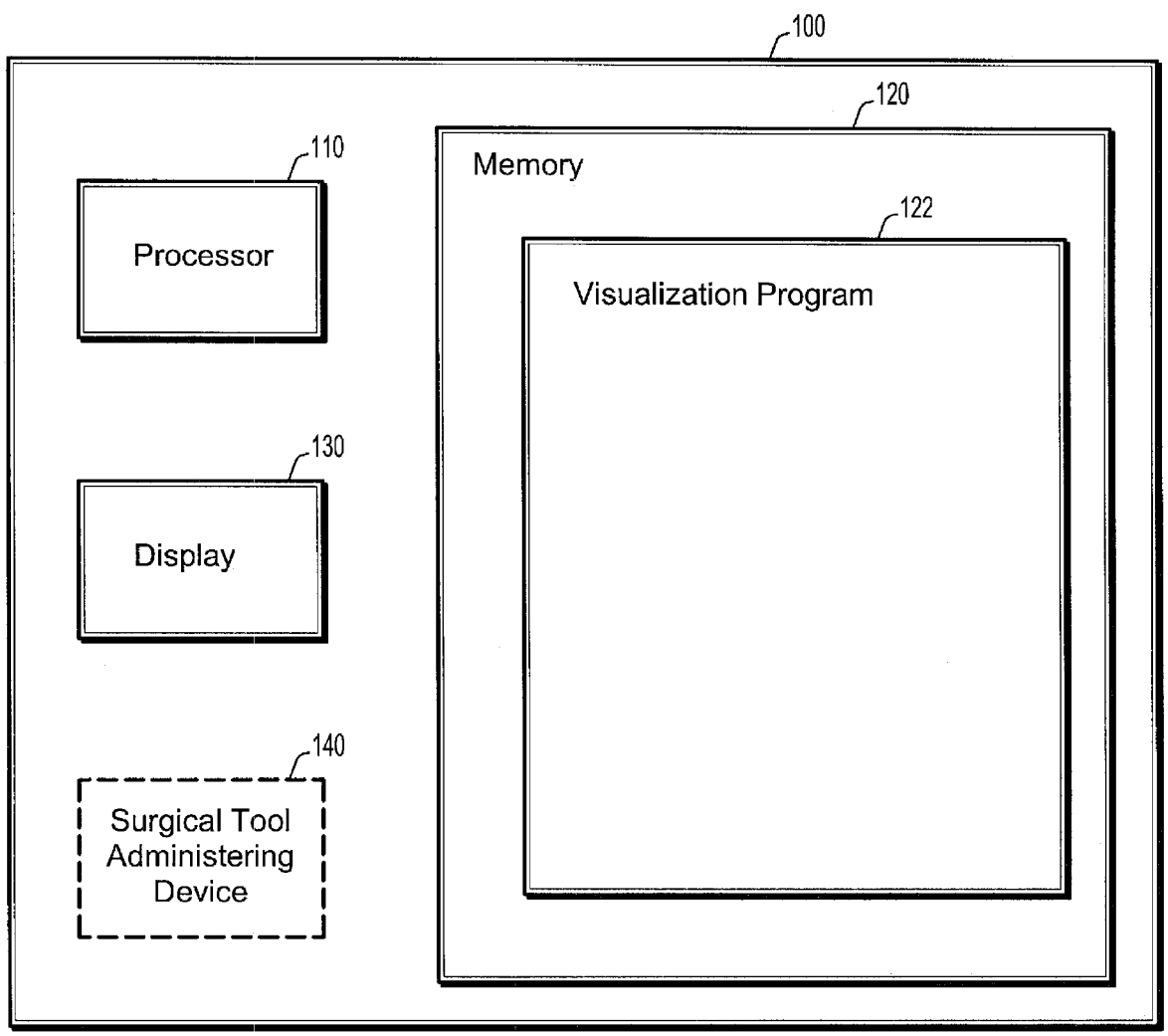
FIG. 1 illustrates a high-level block diagram of a system for visualizing one or more objects of interest within a volume of imaging data according to an exemplary embodiment of the present invention.

FIG. 1 illustrates a high-level block diagram of a system for visualizing one or more objects of interest within a volume of imaging data according to an exemplary embodiment of the present invention.

The system 100 includes a processor 110, a memory 120, and a display 130. A visualization program 122 is stored in the memory 120 and the processor 110 executes the visualization program 122. The visualization program 122 receive a volume of imaging data and displays a new image on the display 130 by adaptively changing the amount of visible information from the volume based on (1) a viewing direction of the volume, (2) a position of one or more objects of interest within the volume, and importance values of materials within the volume.

The system 100 may optionally include a surgical tool administering device 140. For example the surgical tool administering device 140 could be a surgical robot which automatically adjusts the angle, location, and depth that a needle is to be inserted within a patient based on the objects of interest in the new image. One of the objects of interest would then be the needle, and the other could be the structure the needle is to be inserted within. Without such a surgical robot, a user could manually perform a surgical procedure on a patient while being visually guided by a display of the new image. For example, a user could manually insert a needle into a structure of a patient while observing the needle as one of the objects of interests and the structure as another of the objects of interest on a display.

The volume of imaging data can be generated from various types of imaging modalities, such as computed tomography (CT), computed tomography angiography (CTA), magnetic resonance (MR), ultrasonography, positron emission tomography (PET), single photon emission computed tomography (SPECT), magnetic source imaging, etc. The materials may represent different types of anatomical tissue structures within the volume, such as bones, blood vessels, organ tissue, etc. An object of interest occupies a region within the volumetric data set. For example, an object of interest could be the heart in a cardiac CT scan. While it is preferred that the volume of imaging data be provided from medical data, the present invention is not limited thereto. For example, the present invention may be applied to other industries, such as mining, where the materials may be for example, veins of gas, oil, or mineral deposits within the ground.

Figure 2:
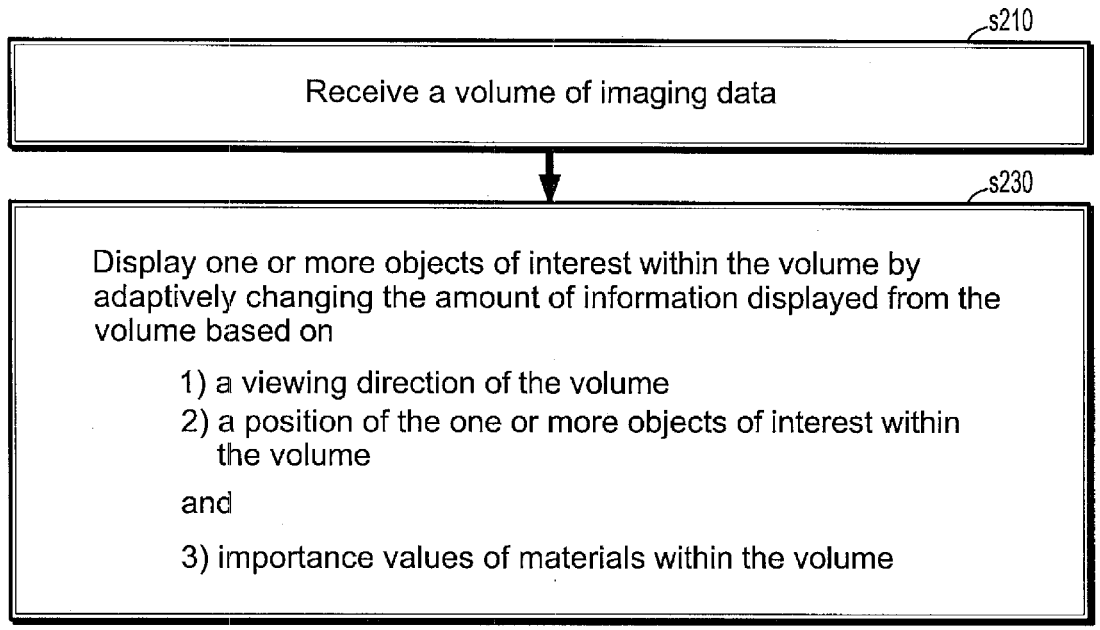
FIG. 2-4 illustrate flow-charts to represent a method for visualizing one or more objects of interest within a volume of imaging data according to an exemplary embodiment of the present invention.
Figure 3:
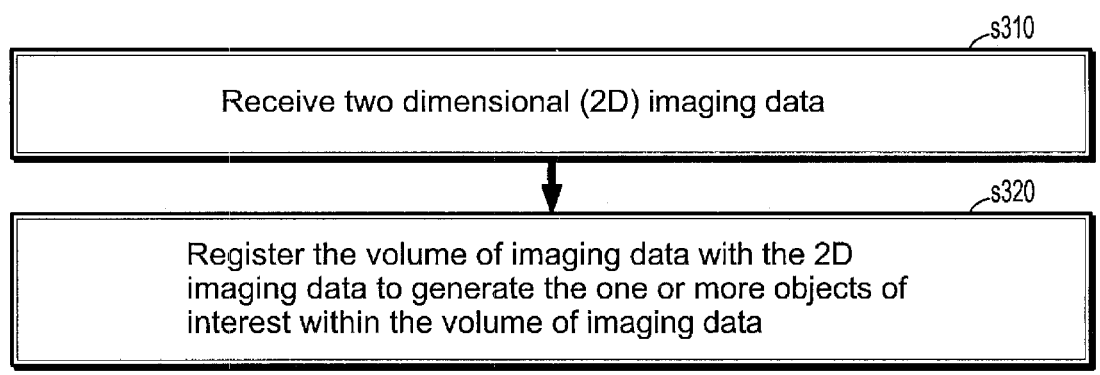
Figure 4:
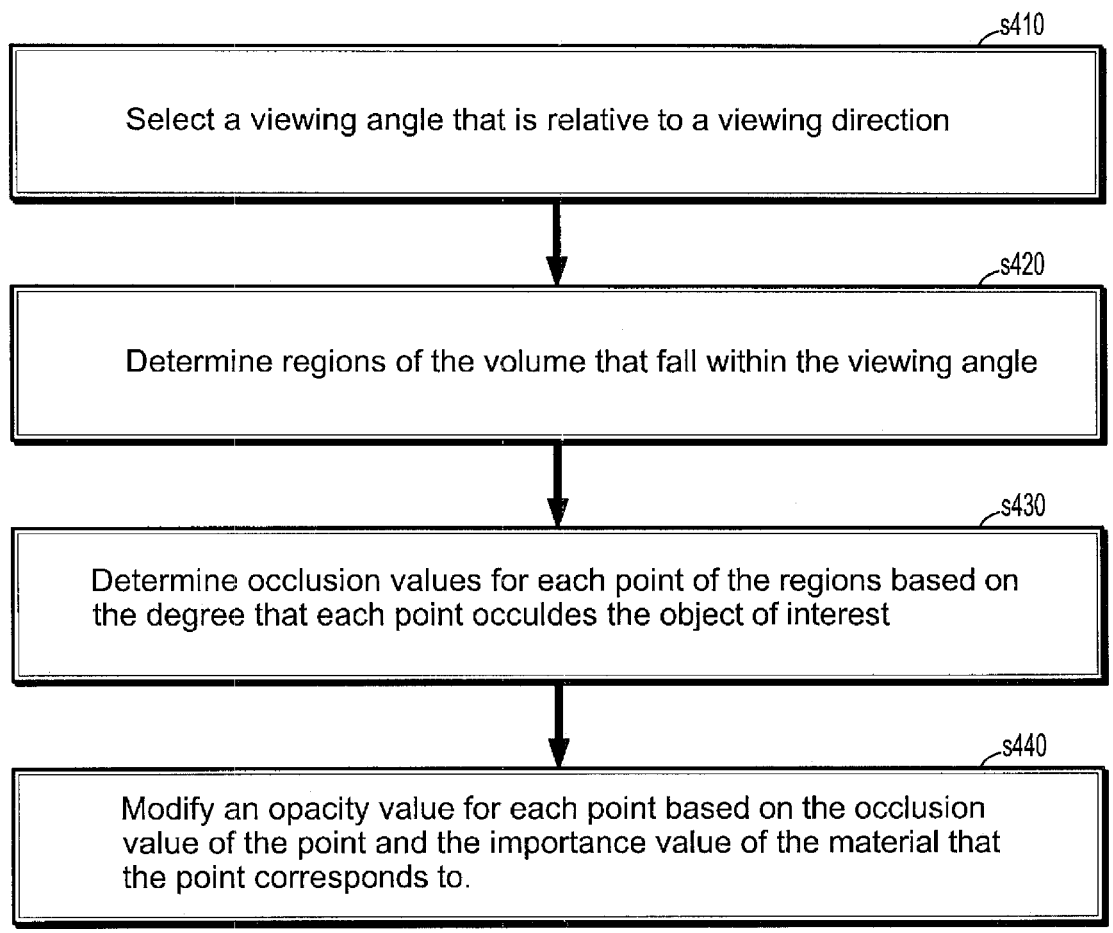

FIG. 2-4 illustrate flow-charts to represent a method for visualizing one or more objects of interest within a volume of imaging data according to an exemplary embodiment of the present invention. Referring to FIG. 2, the method includes receiving a volume of imaging data (s210), and displaying one or more objects of interest within the volume by adaptively changing the amount of information displayed from the volume based on (i) a viewing direction of the volume, (ii) a position of the one or more objects within the volume, (iii) and the user-specified importance values of materials within the volume.

The objects of interest may already be present in the volume. Alternatively, the objects of interest may come from two-dimensional (2D) imaging data, such as, for example, a tracked ultrasound. Referring to FIG. 3, two-dimensional (2D) imaging data is received (s310) and registered with the volume of imaging data to generate the one or more objects of interest within the volume of imaging data (s320). An additional external object of interest could then also be a tracked surgical tool, as pointed out above.

The step of displaying the one or more objects of interest within the volume by adaptively changing the amount of information displayed from the volume based on the above criteria, may be performed using the steps illustrated in FIG. 4. Referring to FIG. 4, a viewing angle is selected that is relative to the viewing direction of the volume (s410). Regions of the volume that fall within the viewing angle are then determined (s420). Occlusion values for each point of the regions are then determined based on the degree that each point occludes the object of interest (s430). The presentation of the volume may then be adjusted by modifying an opacity value for each point based on the occlusion value of the point and the importance value of the material that the point corresponds to (s440).

The determining of the regions may include determining a first region and a second region. The bottom of the first and second region are corresponding first and second distances away from one of the objects of interest, the first distance being less than the second distance. The first and second regions are corresponding first and second angles away from the viewing direction, the first angle being less than the second angle. The first and second regions may be cone shaped.

The importance values may be generated using a transfer function. A standard transfer function assigns a color (r,g,b) and a opacity ($\alpha$) to every sample point in the volume data set. A feature vector $\vec{x}$ is generated from the local properties of a single sample point as defined by equation 1 below:

$$g(\vec{x}) \rightarrow (r,g,b,\alpha) \qquad (1)$$

where the quadruple (r,g,b,$\alpha$) defines the red-green-blue (RGB) color and opacity for the given feature vector g(x). The number of elements for the feature vector defines the complexity of the transfer function. The transfer function can be split into different components which are defined by their color and opacity distribution in the transfer function space. Each of the components may belong to a different material or tissue in the volumetric data set. The idea behind using importance values for the transfer function is to assign a single value to each component of the transfer function.

However, for a single point in the transfer function space, two or more components can overlap each other. This may require a blending of the color, opacity, and importance values. The following equation 2 describes this blending:

$$g(\vec{x}) \rightarrow \left( \frac{\sum_{i=1}^{Ncomp} \vec{c}_i * \alpha_i * I_i}{\sum_{i=1}^{Ncomp} \alpha_i * I_i}, \max \alpha_i, \max I_i \right) \qquad (2)$$

where $I_i$ are the importance values for each component i, and $N_{comp}$ is the number of all components overlapping at a single point. The RGB color components are combined in equation 2 in the vector c. This blending may be done once before the rendering and results in a lookup-table which assigns each point in the transfer function space to a quintuple consisting of RGB color values, an opacity value, and an importance value.

The importance values may be used to modify the optical properties of a sample point in the volume to emphasize important sample points. Emphasis can be made by color, opacity, shading style, etc. By modifying shading style by importance, important materials can be accentuated and unimportant materials can be deemphasized. The importance values can be used to limit contributions of a given shading mode to an output color, so that materials with low importance values are shaded less than materials of high importance values. The strength of this effect, emphasis, is denoted by the parameter E. The output color can be calculated using the following equation 3:

$$\vec{c} = \vec{c}_{shaded} * (1-(E-I*E)) + \vec{c}_{unshaded} * (E-I*E) \qquad (3)$$

where $\vec{c}_{shaded}$ is the color value calculated with a given shading method and $\vec{c}_{unshaded}$ is the color value from the transfer function. When E=1, equation 3 is a linear interpolation between shaded and unshaded colors based on importance, which causes important materials to be fully shaded and unimportant materials to be fully unshaded, suggesting maximum emphasis. When E=0, only the shaded color is used, and all the materials are fully shaded, suggesting no emphasis of important materials.

Figure 5:
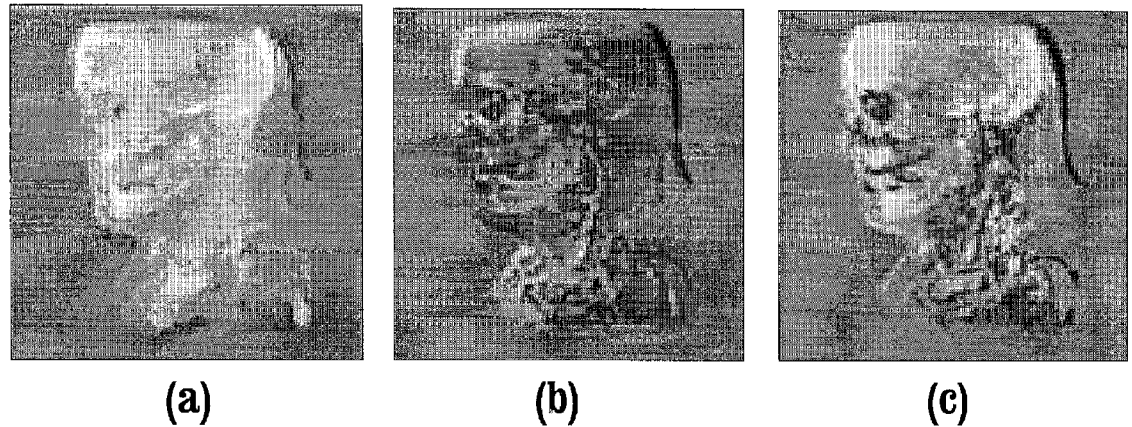
FIG. 5 illustrates the results of importance-driven shading according to an exemplary embodiment of the present invention.

The images in FIG. 5 show how importance-driven shading can emphasize important features. FIG. 5a is not shaded, which results in a very low contrast and spatial perception. FIG. 5b uses Phong shading. Since E=0, vessels in the skull are obscured by shading details on the bone, even though the bone is very transparent. FIG. 5c combines the two images by setting E=1, so that the importance parts (i.e., vessels) are more emphasized and the high-frequency shading information of the non-important parts (i.e., skin or bone) are suppressed. Alternatively, a Gooch shading technique may be used. For example, using Gooch cool-to-warm shading and silhouette enhancement for important materials gives a strong contrast between important and non-important materials, as well as increased-spatial perceptibility.

An object of interest within the volume can be occluded by particular materials within the volume. However, the object can be presented in such a way that the material around it is cut away based on the importance of the material. A simple cutaway view definition partitions space into two distinct regions: the area inside the cutaway, which can be denoted as the clear region, and everything else, which can be denoted as the base. Let an occlusion function, denoted $\Omega$, represent the degree to which a point in space occludes the object of interest. In the simple cutaway scenario, at a given point, $\Omega$=1 if the point is inside the clear region and 0 if it is inside the base region. In eye space, a cutaway surface can be represented by a depth function $\xi(\theta)=z$, where z is the depth of the cutaway surface with angle θ at a given point projected onto the surface. The occlusion function Ω can then be defined for a given point in eye space according to the following equation 4.

$$\Omega = \text{step}(\xi(\theta), p_z) \qquad (4)$$

where $p_z$ is the z component of the point and step (a, x)=0 if x<a and 1 if x≧a. This binary definition suggests rendering can have only two modes: spare (for the clear region) and dense (for the base region). However, to give more control over the rendering of materials with multiple importance values, a new cutaway definition is proposed where occlusion values vary smoothly between 0 and 1 over 3D space.

Figure 6:
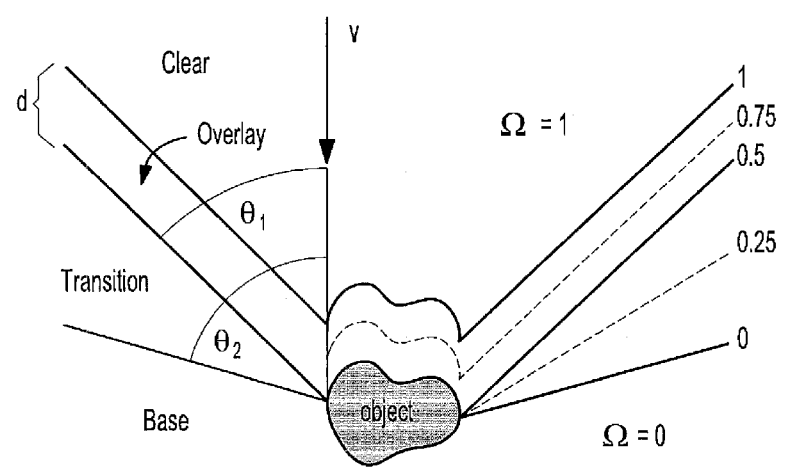
FIG. 6 illustrates the geometric arrangement of an object of interest and contextual cutaways regions according to an exemplary embodiment of the present invention.

FIG. 6, illustrates an object of interest and contextual cutaways regions according to an exemplary embodiment of the present invention. A simple cutaway definition can be modified to include a second cutaway surface, which is defined by a wider angle. This new region is denoted as the transition region. The transition region can have an occlusion function Ω that varies between the two cutout surfaces. Another region, which can be denoted as the overlay region, can be added to control the visibility in the image over the object of interest. The overlay region is bounded by the cutaway surface of $\theta_1$ offset a thickness d towards a camera viewing the volume with a viewing direction V.

Considering these four regions (i.e., the clear, base, transition, and overlay regions), an occlusion function Ω for a given point in eye space is defined according to the following equation 5:

$$\Omega = \frac{\text{ramp}(\xi(\theta_2), \xi(\theta_1), p_z) + \text{ramp}(\xi(\theta_1), \xi(\theta_1)+d, p_z)}{2} \qquad (5)$$

where $\theta_1$ and $\theta_2$ are the cutaway angles, d is the thickness of the overlay region, ramp (a,b,x)=0 if x<a and 1 if x>b, and the ramp is a linear ramp from 0 to 1 for a≦x≦b. Equation 5 results in Ω=0 for points in the base area, Ω=0.5 for points on the transition-overlay boundary, and Ω=1 for points in the clear area, with the appropriate linear blends for points in between the boundaries.

The occlusion function Ω from equation 5 and the previously discussed importance values can be used to render various components of the transfer function in different regions of the cutaway structure. It is preferred that only materials with the very highest importance values be present in the clear region and that materials be rendered more densely in the base region. Materials should be faded out based on their importance such that materials of low importance are cut away at a wider angle than materials of higher importance in the transition region. Materials of moderately high importance may be allowed in the overlay region, where they will be faded out before the clear region.

The opacity of a sample point can be modified based on the occlusion value at that point. To control fading, two occlusion value thresholds $\tau_l$ and $\tau_u$ may be established between which points will be faded. Given the thresholds $\tau_l$ and $\tau_u$, opacity can be modified by the following equation 6:

$$\alpha' = \alpha * (1 - l\text{instep}(\tau_l, \tau_u, \Omega)) \qquad (6)$$

where α is the alpha component of a sample computed from the transfer function for a given point, α' is the alpha component to be used in rendering, and Ω is the occlusion value at the point. If a constant set of τ such as (0,1) is chosen, materials would be completely transparent in the clear region, and opacity would be unchanged in the base region, with a uniform fade in the overlay and transition regions based directly on the occlusion value.

Importance may be incorporated into equation 6 by automatically calculating the thresholds for each sample based on the importance value computed from the transfer function. It is preferred that materials of high importance have sharp fades so their cutaway boundaries are easily visible. It is also preferred that sample points near the cutaway boundary at $\theta_1$, between the overlay and transition regions, be faded so their transition into the clear region is smooth. Materials beyond the beginning of the base region should not be faded.

Figure 7:
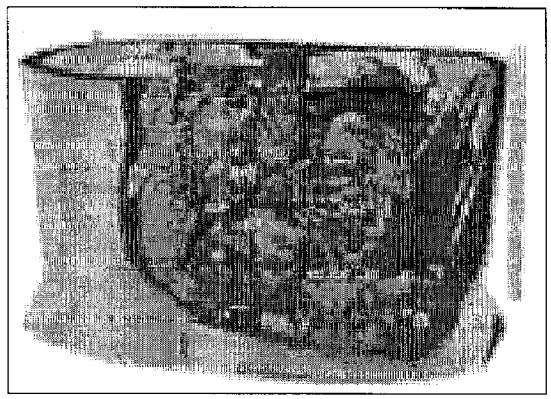
FIG. 7 illustrates visualizations of an object of interest according to an exemplary embodiment of the present invention.
Figure 7:
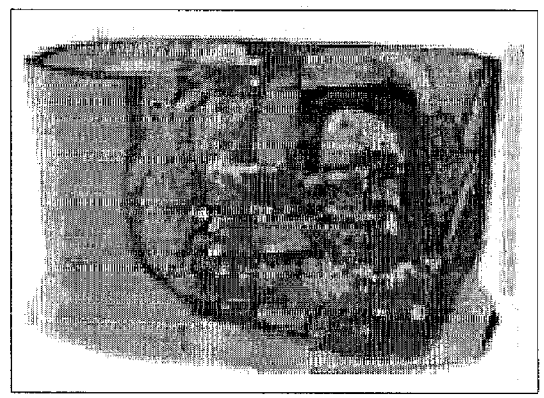

FIG. 7 illustrates visualizations of an object of interest according to an exemplary embodiment of the present invention. FIG. 7 illustrates a CT scan of an abdomen and the object of interest is a plane textured with the volume data and embedded in the volume. The transfer function is defined such that the importance values for skin and flesh are lowest (i.e., 0.1 and 0.01 respectively), vessels and bone are highest (i.e. 0.99), and organs are in between (i.e., 0.5). In FIGS. 7a and 7b, $\theta_2$ is set larger than $\theta_1$. The skin and flesh can be cut away at a wider angle and the organs can be seen fading into the transition region. The thickness d of the overlay region of FIG. 7b is set to be smaller than that of FIG. 7a, so that the vessel and bones are only visible just in front of the plane.

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention as defined by the appended claims.

What is claimed is:

1. A method for visualizing one or more objects of interest within a volume of imaging data, the method steps comprising:

receiving, by a processor, the volume of imaging data; and displaying the one or more objects of interest within the volume by adaptively changing by the processor an amount of information displayed from the volume based on a viewing direction of the volume, a position of the one or more objects of interest within the volume, and importance values of materials within the volume, wherein the displaying comprises:

selecting a viewing angle that is relative to the viewing direction;

determining regions of the volume that fall within the viewing angle by determining a first region having a first angle away from the viewing direction, the first region having a bottom that is a first distance away from the object of interest and determining a second region having a second angle away from the viewing direction, the second region having a bottom that is a second distance away from the object of interest, wherein the first angle is less than the second angle and the first distance is less than the second distance;

determining occlusion values for each point of the regions based on the degree that each point occludes the object of interest; and modifying an opacity value for each point based on the occlusion value of the point and the importance material that the point corresponds to.

2. The method of claim 1, further comprising using the display of the one or more objects of interest within the volume to aid a surgical procedure.

3. The method of claim 2, wherein a first one of the objects of interest is a needle and the surgical procedure comprises guiding the needle into a second one of the objects of interest.

4. The method of claim 1, wherein the receiving the volume of imaging data comprises:
   receiving two dimensional (2D) imaging data; and
   registering the volume of imaging data with the 2D imaging data to generate the one or more objects of interest within the volume of imaging data.

5. The method of claim 1, wherein the volume of imaging data comprises data from a three dimensional (3D) computed tomography (CT) scan.

6. The method of claim 4, wherein the 2D imaging data comprises data from a tracked ultrasound image.

7. The method of claim 1, further comprising shading the materials within the volume based on the corresponding importance values.

8. The method of claim 1, wherein the materials represent different types of anatomical tissue structures within the volume.

9. A method for visualizing an object of interest, the method steps comprising:
   selecting, by a processor, a viewing direction with respect to an object of interest in a volume of image data, and first and second angles with respect to the viewing direction, the second angle being less than the first angle;
   determining, by the processor, a first region within the volume defined by the first angle, a second region within the volume defined by the second angle, and an overlapping region encompassing points of the first region and the second region;
   selecting, by the processor, a first occlusion value for the first region and a second and occlusion value for the second region based on respective amounts that the first and second regions occlude the object of interest; and
   displaying the object of interest by modifying an opacity of a non-overlapping part of the first region based on the first occlusion value, modifying an opacity of the non-overlapping part of the second region based on the second occlusion value, and modifying an opacity of the overlapping region based on a third occlusion value between the first and second occlusion values.

10. The method of claim 9, wherein the opacity of the non-overlapping part of the second region is less than the opacity of the non-overlapping part of the first region.

11. The method of claim 10, wherein the opacity of the non-overlapping part of the second region is entirely clear.

12. The method of claim 9, wherein the first region is a cone.

13. The method of claim 12, wherein the apex of the cone contacts the object of interest.

* * * * *